(12) United States Patent
Seman

(10) Patent No.: US 6,436,658 B1
(45) Date of Patent: *Aug. 20, 2002

(54) METHOD FOR THE DETERMINATION OF HOMOCYSTEINE

(75) Inventor: Leo Seman, Salem, NH (US)

(73) Assignee: Genzyme Corporation, Cambridge, MA (US)

(*) Notice: Subject to any disclaimer, the term of this patent is extended or adjusted under 35 U.S.C. 154(b) by 184 days.

This patent is subject to a terminal disclaimer.

(21) Appl. No.: 09/605,685

(22) Filed: Jun. 26, 2000

Related U.S. Application Data

(63) Continuation of application No. 09/440,001, filed on Nov. 12, 1999, now Pat. No. 6,174,696.
(60) Provisional application No. 60/108,099, filed on Nov. 12, 1998.

(51) Int. Cl.[7] .............................. C12Q 1/34; C12Q 1/52; C12Q 1/00

(52) U.S. Cl. .............................. 435/18; 435/16; 435/4; 435/23; 435/24; 435/7.1

(58) Field of Search .............................. 435/18, 16, 4, 435/23, 24, 7.1

(56) References Cited

U.S. PATENT DOCUMENTS

| | | | |
|---|---|---|---|
| 4,940,658 A | 7/1990 | Allen et al. | 435/18 |
| 5,374,560 A | 12/1994 | Allen et al. | 435/18 |
| 5,438,017 A | 8/1995 | Allen et al. | 435/18 |
| 5,457,055 A | 10/1995 | Allen et al. | 435/18 |
| 5,478,729 A | 12/1995 | Van Atta et al. | 435/18 |
| 5,523,225 A | 6/1996 | Kraus | 435/18 |
| 5,631,127 A | 5/1997 | Sundrehagen | 435/18 |
| 5,715,835 A | 2/1998 | Lishko et al. | 435/18 |
| 5,827,645 A | 10/1998 | Sundrehagen | 435/18 |
| 5,958,717 A | 9/1999 | Sundrehagen | 435/18 |
| 6,046,017 A | 4/2000 | Schirch | 435/25 |
| 6,063,581 A | 5/2000 | Axis-Shield | 435/18 |
| 6,066,467 A | 5/2000 | Xu et al. | 435/23 |
| 6,174,696 B1 * | 1/2001 | Seman | 435/18 |

FOREIGN PATENT DOCUMENTS

| | | |
|---|---|---|
| WO | WO 98/07872 | 2/1998 |
| WO | WO 99/05311 | 2/1999 |

OTHER PUBLICATIONS

Axis—Immunoassay for the measurement of Plasma Homocysteine;source unknown.
"Bringing HomocysteineInto Your Lab", *Clinical Laboratory Strategies* (Sep. 1998) 3:9 1–2.
Dudman, Nicholas P.B. et al., "Enzyme conversion immunoassay for determining total homocysteine in plasma or serum", *Clinical Chemistry*, (1998) 44:2 pp. 311–316.
Frantzen, Frank et al., "Enzyme conversion immunoassay for determining total homocysteine in plasma or serum", *Clinical Chemistry*, (1998) 44:2 pp. 311–316.
Garg, Uttam C. et al., "Short–term and long–term variability of plasma homocysteine measurement", *Clinical Chemistry*, (1997) 43:1 pp. 141–145.
Hankey, Graeme J. and Eikelboom,John W., "Homocysteineand Vascular Disease" *The Lancet*, (Jul. 31, 1999) 354: pp. 407–413.

(List continued on next page.)

*Primary Examiner*—Louise N. Leary
(74) *Attorney, Agent, or Firm*—Jennifer L. Duré

(57) ABSTRACT

The invention relates to a method for determining homocysteine concentration in samples in which homocysteine is condensed using an enzyme cystathionine β sythase to form cystathionine. Pyruvate and/or ammonia are released from cystathionine by action of an enzyme, cystathionine β lyase, and homocysteine is regenerated. The release of pyruvate and/or ammonia can be correlated to the concentration of homocysteine present in the sample.

20 Claims, 2 Drawing Sheets

OTHER PUBLICATIONS

Malinow, M. Rene, "Plasma Homocyst(e)ine and Arterial Occlusive Diseases: A Mini–Review", *Clinical Chemistry*, (1994) 40:1, pp. 173–176.

McCully, Kilmer S., "Homocysteine and Vascular Disease", *Nature Medicine*, (Apr. 1996) 2:4 pp. 386–389.

PCT/US99/26989 International Search Report.

Selhub, Jacob and Miller, Joshua W., "The pathogenesis of homocysteinemia: interruption of the coordinate regulation by S–adenosylmethionine of the remethylation and transsulfuration of homocysteine 1–4", *American Society for Clinical Nutrition* (1992), 55: pp. 131–138.

Shipchandler, Mohammed T. and Moore, Edwin G., "Rapid, Fully Automated Measurement of Plasma Homocyst(e)ine with the Abbott IMx Analyzer", *Clinical Chemistry*, (1995) 41:7 pp. 991–993.

Stampfer, M. et al., "A Prospective Study of Plasma Homocyst(e)ine and Risk of Myocardial Infarction in US Physicians", *Journal of the American Medical Association*, (Aug. 19, 1992) 268:7 pp. 877–881.

* cited by examiner

SEQUENCE LISTING

<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
gggaattcca tatggcggac aaaaagcttg atactc                     36

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
cgcggatcca aaagtggcaa tgttatacaa ttcgcgc                    37

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:

```
        Oligonucleotide primer

<400> SEQUENCE: 3
tggcccgggg cggacaaaaa gcttgatact caactg                                36

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
gggggatcca aaagtggcaa tgt                                              23

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5 tgcccggga ctaaatctga gcagcaagcc gattca                                 36

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
gggggatcct tatgctaagt agctcag                                          27
```

METHOD FOR THE DETERMINATION OF HOMOCYSTEINE

This application claims the benefit of U.S. Provisional Patent Application Ser. No. 60/108,099, filed Nov. 12, 1998. This is a continuation of U.S. patent application Ser. No. 09/440,001, filed Nov. 12, 1999 now issued as U.S. Pat. No. 6,174,696.

BACKGROUND OF THE INVENTION

Total concentration of homocysteine in body fluids, such as plasma or serum, is an important marker for disease. For example, homocysteine quantification can be an important risk indicator for cardiovascular disease, can be a sensitive marker of cobalamin and folate deficiencies, and can be used to diagnose in-born errors in metabolism known as homocystinuria. Homocysteine quantification has also been reported as useful in assessing birth defects in pregnant women and cognitive impairment in the elderly. See Frantzen, et al., *Enzyme Conversion Immunoassay for Determining Total Homocysteine in Plasma or Serum*, Clinical Chemistry 44:2, 311–316 (1998). Current assays, such as those using HPLC or GC-MS, are expensive and require highly skilled technical staff. An efficient and accurate assay, that can be carried out without necessity for highly skilled personnel or complex analytical chemistry equipment, has been needed.

SUMMARY OF THE INVENTION

The present invention provides an assay for homocysteine found in plasma, serum or other body fluids of a patient. According to this assay, a homocysteine containing sample is condensed using an enzyme, cystathionine β-synthase, to form cystathionine. This cystathionine is subjected to another enzyme, cystathionine β-lyase, to release pyruvate and ammonia, and homocysteine. The total homocysteine concentration in the patient sample can be determined based on the detection and correlation of the pyruvate and/or ammonia released.

In another embodiment of the invention, the patient sample is subjected to treatment by dithiothreitol or other reducing agent, in appropriate amounts to produce free homocysteine in the sample.

In a still further embodiment, the enzymes cystathionine β-synthase and cystathionine β-lyase may be treated with a phosphorylated form of vitamin B6 in order to optimize their function in the assay of the invention.

A still further embodiment of the present invention is a kit for determining homocysteine concentration in a sample that includes the enzymes cystathionine β-synthase and cystathionine β-lyase, and serine. Such kit may further include a reducing agent such as dithiothreitol (DTT), and an enzyme co-factor such as pyridoxal 5' phosphate (PLP).

DETAILED DESCRIPTION OF THE INVENTION

Figure 1:
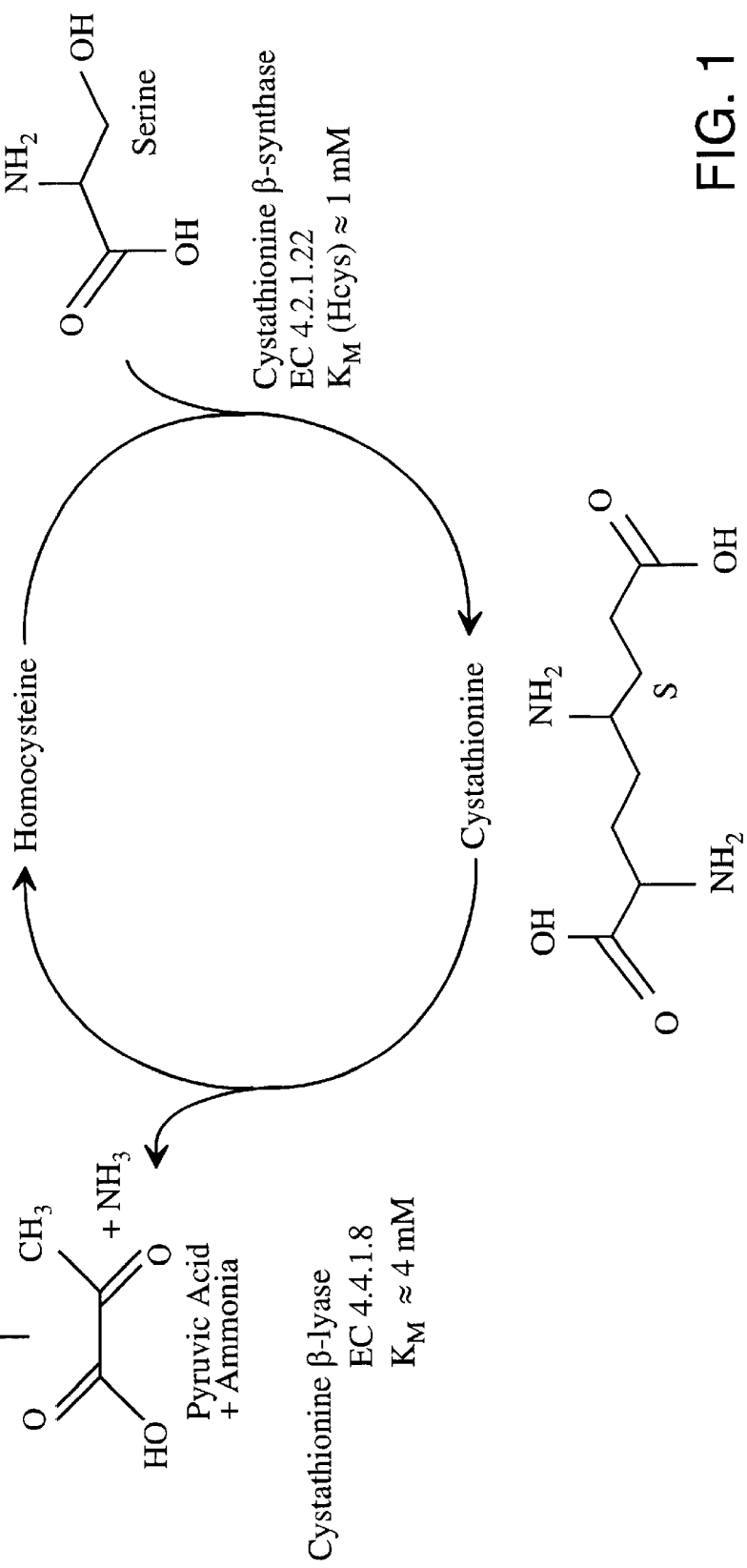
FIG. 1 illustrates an assay method for homocysteine according to the invention.

The measurement of total plasma homocysteine from plasma, serum, or other body fluids can be performed by condensing homocysteine with serine to form cystathionine, by a beta substitution reaction, using the enzyme cystathionine β-synthase (CBS) (enzyme classification [EC]4.2.1.22). The cystationine then undergoes a beta elimination reaction catalyzed by cystathionine β-lyase (CBL) (EC 4.4.1.8), releasing pyruvate and/or ammonia, and regenerating homocysteine. The regenerated homocysteine will then be free to be condensed with another serine molecule by CBS, EC 4.2.1.22, and again to form cystathionine, and again release pyruvate and ammonia by beta elimination with CBL, EC 4.4.1.8.

This recycling will continue at a rate determined by the concentration of total homocysteine in the plasma or serum sample. At the low concentrations of homocysteine found in plasma and serum, the reaction rate is slow and very linear to homocysteine concentration. The Michaelis-Menten constants (Km) for the two enzyme activities described exist in nature in the $10^{-3}$ moles/liter range, while plasma and serum tend to be in the $10^{-5}$ moles/liter range. This dictates the slow linear correlation between reaction rate and plasma concentration. By measuring the production of pyruvate and/or ammonia over a fixed length of time, the reaction rate can be determined and related to the total homocysteine concentration in the sample.

There are many ways of determining the presence of ammonia and/or pyruvate by standard commercially available diagnostic reagent methods. Although homocysteine occurs in very low concentrations in plasma, for example, sensitivity can be overcome by cycling the reaction in the presence of serine until an adequate amount of pyruvate and/or ammonia is produced to be accurately measured by the commercially-available, selected method(s).

Homocysteine is found in body fluids mostly in the form of molecules covalently disulfide-linked to another compound. In this regard, homocysteine may be found bound to another homocysteine molecule (forming homocystine), to a cysteine molecule, or a cysteine residue in a protein molecule. Seventy percent of homocysteine is disulfide linked to a cysteine residue on an albumin molecule. Only one percent (1%) of all homocysteine exists as unbound molecules that are not disulfide-linked to another molecule. Therefore, to optimize the enzyme reactions described above, homocysteine molecules should be liberated from their disulfide interactions and permitted to exist as free homocysteine. This can be achieved by reducing the disulfide bonds. One of the easiest ways to facilitate this is with a chemical reducing agent, such as dithiothreitol (DTT), although there are many such chemical agents available that would also reduce the disulfide bonds adequately. This compound should be present in the lowest possible concentration to disrupt the disulfide bonds without interfering with the functions of enzymes in the enzyme cycle or the assays to determine pyruvate and/or ammonia. High levels of DTT, for example, can interfere with analytical reagents and prevent the conduct of the assay. In this regard, the homocysteine recycling enzymes can generally tolerate concentrations of DTT up to approximately 30 millimolar. More preferably, and depending on the detection method used, the reduction of homocysteine disulfide interaction may be accomplished with an amount of DTT approximately up to 10 millimolar, and most preferably 2 to 10 millimolar DTT.

Optimal function of the enzymes that recycle homocysteine, as described above with respect to CBS, EC 4.2.1.22, and CBL, EC 4.4.1.8, can be obtained with the use of low concentrations of an enzyme co-factor, such as pyridoxal 5' phosphate (PLP), a phosphorylated form of vitamin B6. These enzymes have a Km for PLP of $5 \times 10^{-6}$ moles/L and therefore, about a 5 micromolar concentration of PLP can typically be used. However, it will be understood that other amounts of PLP, and other enzyme co-factors having similar characteristics, may be used in order to carry out the assay of this invention.

FIG. 1 illustrates the cyclic reaction that permits the measurement of homocysteine according to the invention.

In one embodiment of the invention, free homocysteine is condensed with serine to form cystathionine using CBS, EC 4.2.1.22. The cystathionine is then treated with CBL, EC 4.4.1.8 to release pyruvate and ammonia and regenerate homocysteine.

In another embodiment, the use of DTT, or other reducing agent, in an appropriate amount facilitates the production of free homocysteine, protein and cysteine from bound protein samples. This homocysteine is then available for condensation with serine and treatment with CBS, EC 4.2.1.22. Preferably, PLP may also be added to this reaction mixture. Optimally, PLP may further be added to the cystathionine and CBL, EC 4.4.1.8. An example of these optimized reactions may be written as follows:

(1) (a sample containing any or all of homocysteine disulfide linked to protein, homocystine, homocysteine and homocysteine bound to cysteine)+DTT=free homocysteine+protein+cysteine+oxidized DTT;

(2) free homocysteine+serine+PLP+CBS=cystathionine+ PLP+CBS;

(3) cystathionine+PLP+CBL=free homocysteine+ pyruvate+ammonia.

These steps are repeated to produce sufficient amounts of pyruvate and/or ammonia to permit measurement.

After a fixed period of time, pyruvate and/or ammonia are measured using a commercially available assay. In this regard, pyruvate and/or ammonia detection may be accomplished with pyruvate oxidase, lactate dehydrogenase or an ammonia reagent. It will be understood that other methods for detecting pyruvate and/or ammonia concentrations could also be used.

By conducting these reactions of the invention cyclicly, measurements may be made of pyruvate and/or ammonia production over time, which can then be correlated to the total homocysteine concentration in the sample.

Detection of total homocysteine can be accomplished as follows:

To a 100 microliter sample of plasma, serum, or other body fluid, is added 10 millimoles of dithiothreitol, one microunit of CBS, one microunit of CBL, 5 micromoles of PLP and 1 millimole serine. Also added are the commercially available reagents for the calorimetric detection of pyruvate and/or ammonia. At time zero, pyruvate and/or ammonia are measured according to specifications of the commercial reagents. Then, the sample is allowed to incubate in a temperature controlled chamber (at approximately 37° C.) for 10 minutes, and then pyruvate and/or ammonia are again measured. This procedure may need to be performed several times until an adequate amount of pyruvate and/or ammonia has accumulated for an accurate reading. Once a length of time has been established that will reproducibly measure an amount of pyruvate and/or ammonia that is suitable for the sensitivity of the respective commercial kits, then samples will always be incubated for that length of time. A correlation between homocysteine and pyruvate and/or ammonia will be established with a series of standards of known homocysteine values in plasma and a linear curve will be established. The unknown sample will be determined by linear regression.

The present invention also provides a diagnostic kit for determining homocysteine concentration in a sample, which contains the enzymes cystathionine β-synthase and cystathionine β-lyase, and serine. The kit may further include a reducing agent, such as DTT, and enzyme co-factor, such as PLP.

EXAMPLES

I. The CBL Enzymes

A. Procedure for Cloning CBL

The pLC414 plasmid carrying the metC gene was isolated from ATCC Clone #37384 (J. R. Uren, Proc. Natl. Acad.Sci. USA 68: 367–371, 1971) using techniques described in Maniatis et al., Molecular Cloning, A Laboratory Manual, 2d, Cold Spring Harbor Laboratory Press (1989). The metC gene was cloned from the plasmid by PCR using primers synthesized according to the published DNA sequence. In addition, restriction enzyme sites were added at the N-and C-termini that were suitable for cloning the metC cDNA into an appropriate expression vector. PCR primers were synthesized and had the following 5'-3' sequences: Forward Primer (added an Nde I site at the ATG start codon of metC) GGG AAT TCC ATA TGG CGG ACA AAA AGC TTG ATA CTC (SEQ ID NO: 1) Reverse Primer—(added a BamH1 site after the stop codon of metC) CGC GGA TCC AAA AGT GGC AAT GTT ATA CAA TTC GCG C (SEQ ID NO: 2). The PCR products were digested with Nde I and BamH I and ligated into a lac promoter expression vector (pGB3Nde of Genzyme Corporation, Cambridge, Mass.) which had been digested with the same enzymes. The resulting plasmid was then transformed into Top 10 *E. Coli* cells (Invitrogen) following the protocol provided with the cells. The transformants were plated on LB agar+50 μg/ml carbenicillin+0.5% glucose and grown overnight. Colonies were screened for the presence of the appropriate plasmid and enzyme activity.

The pGB3Nde vector of Genzyme Corporation is described, in part, as "pGB3" in U.S. Pat. No. 5,236,838. The described pGB3 vector has been modified to add an Nde, forming the presently employed vector designated pGB3Nde. Methodology for modification of a vector in this manner may be found in T. Maniatis, E. Fritsch, and J. Sambrook, Molecular Cloning, A Laboratory Manual, 2d ed., Cold Spring Harbor Press (1989), and F. M. Ausubel et al., Current Protocols in Molecular Biology, Green Publishing Associates and Wiley-Interscience (1989). It will be appreciated that other similar base vectors, such as may be available from Stratagene, La Jolla, Calif., can also be employed.

B. Procedure for Purification of CBL

The purification procedure used for CBL is an adaptation of a published procedure (Dwivedi, C. M., Biochemistry 1982, 21, 3064–3069). Cultures from a CBL clone were grown and expression of CBL was induced with isopropyl thiogalactoside (IPTG). The cell suspension was centrifuged and the resulting cell pellet was lysed using 1 mg/ml lysozyme on ice for 15 minutes, followed by sonication. The lysate was loaded onto a Q Sepharose FF (Pharmacia) column and eluted with a salt gradient (0–0.5 M sodium chloride). Active fractions were purified on a hydroxyapatite column (Macro-Prep Ceramic Hydroxyapatite TYPE 1 40 μM from BioRad) and eluted with a phosphate gradient (10–400 mM potassium phosphate, pH 6.8). The eluate was loaded onto a Blue Sepharose CL-6B column (Pharmacia) and the CBL eluted with a salt gradient (0–1.0 M sodium chloride). A Mono Q column (Pharmacia) was used to concentrate the enzyme. The fractions with activity were pooled, diluted with glycerol to 50% and stored at −20° C.

An alternative procedure for cloning and purification of the CBL enzyme is described below.

C. Procedure for Cloning CBL-MBP Protein Fusion

The CBL gene was cloned from an expression vector (pGB3Nde) into the pMAL-c2X vector (New England Biolabs) to create an MBP (maltose binding protein) Fusion Protein. PCR primers were designed and synthesized to clone the CBL open reading frame and add a Sma I site at the N-terminus. The Forward Primer had the following 5'-3' sequence: TGG CCC GGG GCG GAC AAA AAG CTT GAT ACT CAA CTG (SEQ ID NO: 3). The addition of this site resulted in the first methionine in the CBL sequence to be replaced by a glycine. The Reverse Primer had the following 5'-3' sequence: GGG GGA TCC AAA AGT GGC AAT GT (SEQ ID NO: 4). The PCR products were digested with Sma I and Bam HI and ligated into the pMAL-c2X vector which had been digested with Xmn I and Bam HI. The resulting plasmid was then transformed into Top 10 *E coli* cells (Invitrogen) following the protocol provided with the cells. The transformants were plated on LB agar+50 μg/mL carbenicillin+0.5% glucose and grown overnight. Colonies were screened for the presence of the appropriate plasmid and CBL activity.

D. Procedure for Purification of CBL-MBP

Cultures from a CBL-MBP clone were grown and expression of CBL-MBP was induced with IPTG. The cell suspension was centrifuged and the resulting cell pellet was lysed using 1 mg/mL lysozyme and 150 U/mL of DNAse I. The lysate was loaded onto an Amylose column (New England Biolabs) and eluted with a buffer containing 10 mM maltose. Active fractions were pooled, diluted with glycerol and stored at −20° C.

E. DTNB Assay for Cystathionine β Lyase

Assay Principle

Cysteine, homocysteine or similar thiols are produced by enzymatic cleavage of cystathionine (CTT), djenkolic acid (DJA) or other thioether substrates. The thiols undergo a disulfide exchange with the aromatic disulfide 5,5'-dithio-bis(2-nitrobenzoic acid) (DTNB) which releases one equivalent of the chromophore 2-nitrobenzoic acid-5-mercaptide (TNB). The release of TNB is followed spectrophotometrically and the reaction rate is calculated from the slope of the absorbance at 410 nm over time using a molar extinction coefficient of 13,200 $M^{-1}$ $cm^{-1}$ for TNB:

Reagents:

5,5'-dithio-bis(2-nitrobenzoic acid) (Sigma D-8130)
L-(+)-cystathionine (Sigma C-7505)
L-djenkolic acid (Sigma D-9255)
Tris (base) (J. T. Baker 4109-02)
dithiothreitol (DTT) (EM Science 11474-4)
pyridoxal 5' phosphate (PLP) (Sigma P-9255)
bovine serum albumin (BSA) (Sigma A-3059)
Hydrochloric acid (HCl) reagent grade
Mono-and dibasic potassium phosphates, reagent grade Stock Solutions:

Assay buffer: 0.1 M Tris-HCl buffer, pH 9.0. Store sterile at room temperature.

Substrate solution: 10 mM L-djenkolic acid or L-(+)-cystathionine in 0.01 N HCl. Suspend solid in HCl, warm container in hot water briefly, mix or sonicate until dissolved, let cool to room temperature. Store at −20° C., reheat after thawing for complete dissolution.

DTNB Solution: 10 mM DTNB in 0.1 M potassium phosphate buffer, pH 7.0. Store at −20° C. Enzyme dilution buffer: 10 mM potassium phosphate buffer, pH 7.0, 100 μM DTT, 10 μM PLP, 10 g/L BSA.

Assay Procedure:

Make up the following amount of reagent cocktail at room temperature for one 96-well plate:

| | |
|---|---|
| 15.6 mL | assay buffer |
| 4.0 mL | substrate solution |
| 0.4 mL | DTNB solution |

Dilute the enzyme samples to be assayed as required with enzyme dilution buffer and keep on ice. The enzyme concentration should be between 0.02 and 25 U/mL. Aliquot 200 μL of reagent cocktail into each well of a flat-bottom 96-well assay plate. Set up microwell plate reader for 10 min kinetic reading at 410 nm, OD range 0–2. Rapidly add 1 to 10 μL of prediluted enzyme samples to assay plate and mix. Immediately transfer plate into reader and start kinetic program.

Unit Definition

For experimental simplicity an enzyme unit is defined as the amount of enzyme that catalyzes the formation of one mole of free thiol per minute from L-djenkolic acid at room temperature. Cystathionine is cleaved by most lyases at similar rates to L-djenkolic acid but some enzyme specific differences occur. A difference in activity can result from assaying at 37° C. as described in some published procedures.

Detection Limits

The minimum amount of enzyme to be added to the assay is estimated as about 10 μL of a 0.01 U/mL solution, which would result in a measurement of 10 mOD/min. Conversely, the estimated maximum photometer rate of 150 mOD/min over 10 mininutes would be achieved by adding 1 μL of a 14 U/mL stock. Adjustments to minimum and maximum amounts with vary according to the detection method employed.

II. The CBS Enzymes

A. Procedure for Cloning CBS

The CBS gene was cloned from *Saccharomyces cerevesiae* genomic DNA. PCR was performed using primers which encoded an Nde I site on the 5' end and a BamH I site on the 3' end. The amplicon was digested with these restriction enzymes and then ligated into an expression vector (pGB3Nde) which was digested with the same restriction enzymes. The plasmid was then transformed into Top 10 *E coli* cells (Invitrogen) and plated on selective media. The colonies were selected that contained a plasmid of the appropriate size.

An expression experiment was performed to determine if CBS activity was present in the clones. The cultures of the clones were grown in selective media with thiamine and aminolevulinate. IPTG was added for 4 hours and 21 hours to induce protein production. The cell pellets were lysed with lysozyme and DNase and the lysate supernatant was assayed for CBS activity using the radioactive assay described by Jan Kraus in Kraus, J P, Cystathionine β-Synthase (human), Methods Enzymol. 143, 388–394 (1987) (hereinafter "Kraus publication"), and the ninhydrin assay to detect if cystathionine (CTT) was formed by incubating the lysate with serine and homocysteine. By both assays, lysate expressed CBS activity.

B. Procedure for Purification of CBS

Based on the sequencing and expression results, the clone was selected for purification which has activity and has no error in the sequence side by side comparing with the Kraus publication.

The CBS clone was grown in Terrific Broth (TB) with 50 μg carbenicillin, 0.001% thiamine and 0.3 mM aminolevulinic acid (ALA) at 30° C. 1 mM IPTG was added and the culture was incubated for 21 hours at 30° C. Cells were pelleted by centrifugation for eight minutes at 8000 RPM. The cell pellets were resuspended in 50 mM Tris-HCl, pH 8.0 containing 10 μM pyridoxal 5' phosphate (PLP) and spun again. The cell pellet was frozen until ready for lysis and purification. The cell pellet was thawed quickly in a 37° C. waterbath and resuspended in the lysis buffer containing 50 mM Tris-HCl, pH 8.0, 10 μM PLP, 1 mM $MgCl_2$, 0.1 mM DTT, 1 mg/ml lysozyme and 100 units/ml DNase 1. To the lysate, 2 mM EDTA was added and it was centrifuged. The supernatant was placed in ice and while stirring, ammonium sulfate was added slowly to a final concentration of 30%. The suspension was stirred for 30 minutes and centrifuged. Ammonium sulfate was added to the supernatant to a final concentration of 70% and after stirring for 1 hour in ice, the suspension was centrifuged. The pellet was resuspended in the buffer containing 50 mM Tris-HCl, pH 7.5 and 10 μM PLP and dialyzed against the same buffer. The dialysate was loaded onto a MonoQ column which was equilibrated with the same dialysis buffer. The CBS was eluted off the column with a gradient from 0–1 M NaCl. Fractions were assayed for CBS activity using the radioactive assay described in the Kraus publication, and also using the results of the cyclic method of the invention. Those containing activity were pooled and stored at −20° C.

An alternative procedure for cloning and purification of the CBL enzyme is described below.

C. Procedure for Cloning CBS-MBP Protein Fusion

The CBS gene was subsequently cloned from an expression vector (pGB3Nde) into the pMAL-c2X vector (New England Biolabs) to create an MBP (maltose binding protein) Fusion Protein. PCR primers were designed and synthesized to clone the CBS open reading frame and add a Sma I site at the N-terminus. The Forward Primer had the following 5'-3' sequence: TGG CCC GGG ACT AAA TCT GAG CAG CAA GCC GAT TCA (SEQ ID NO: 5). The addition of this site resulted in the first methionine in the CBS sequence being replaced by a glycine. The Reverse Primer had the following 5'-3' sequence: GGG GGA TCC TTA TGC TAA GTA GCT CAG (SEQ ID NO: 6). The PCR products were digested with Sma I and Bam HI and ligated into the pMAL-c2X vector which had been digested with Xmn I and Bam HI. The resulting plasmid was then transformed into Top 10 E. coli cells (Invitrogen) following the protocol provided with the cells. The transformants were plated on LB agar+50 μg/mL carbenicillin+0.5% glucose and grown overnight. Colonies were screened for the presence of the appropriate plasmid and CBS activity.

D. Procedure for Purification of CBS-MBP

Cultures from a CBS-MBP clone were grown and expression of CBS-MBP was induced with IPTG. The cell suspension was centrifuged and the resulting cell pellet was lysed using 1 mg/mL lysozyme and 150 U/mL of DNAse I. The lysate was loaded onto an Amylose column (New England Biolabs) and eluted with a buffer containing 10 mM maltose. Active fractions were pooled and stored at −80° C.

E. Cystathionine β Synthase Assay

1. A First Embodiment

Reagents:
Tris-HCl, 1 M, p H 8.6
Bovine Serum Albumin, 25 mg/ml
Serine, 0.1 M
Pyridoxal 5' phosphate (PLP), 10 mM
Dithiothreitol, 0.2 M
NaOH, 5 M
HCl, 5 M Homocysteine Mixture:

| | |
|---|---|
| Homocysteine thiolactone | 30.72 mg |
| NaOH (5M) | 245 μl |

Dissolve homocysteine thiolactone in NaOH. Incubate 5 min at 37° C. to break the ring. Next add:

| | |
|---|---|
| Tris (1M, pH 8.6) | 100 μl |
| DTT (0.2M) | 100 μl |
| $H_2O$ | 355 μl |
| HCl (5N) | 200 μl |

Check pH with pH paper and adjust to 8.5 if necessary.
This solution is stable for 24 hours at 4° C.

Assay Mixture:

| Stock | Amount |
|---|---|
| 1M Tris pH 8.0 | 10.0 μl |
| BSA 25 mg/ml | 2.0 μl |
| 0.1M Serine | 5.0 μl |
| 10 mM PLP | 10.0 μl |
| 0.2M hcy | 7.5 μl |
| $C^{14}$ Serine | 1.0 μl |
| $dH_2O$ | 59.5 μl |
| Total | 95.0 μl |

Multiply each amount times the total number of samples to be assayed. Store the assay mixture on ice prior to use.

Enzyme Sample

Dilute enzyme sample to CBS specific protein concentration of 1 mg/ml with 10 mM Tris pH 8.0. Glycerol may also be used in place of Tris.

With glass tubes (≈5 ml volume) on ice, add 95 μl of assay mixture to each tube, including the blank.

Add 5 μl of enzyme sample to each tube (or amount to equal 2–5 μg) except the blank, add 5 μl dH2O to blank.

Place the rack containing the tubes in a 37° C. water bath and shake slowly for 30 minutes.

While the reaction is running, prepare a sheet of Whatman #3 chromatography paper, marking lanes for each sample, 3 cm wide.

Terminate the reaction by chilling the tubes in ice water.

Take a 5 μg sample of 3 random assays, spot each onto a small square of assay paper, put these into scintillation vials, set aside until chromatogram is done. Spot 20 μl of the reaction on the paper in the middle 1 cm of each lane. Let the paper dry. Spot 5 μl of cystathionine/serine standard on each end lane of the paper. Place the papers in a chromatography tank.

Develop the chromatogram overnight (or appropriate time for size of the paper) using the following solvents:

| | |
|---|---|
| Isopropanol | 160 ml |
| Water | 40 ml |
| Formic acid | 12 ml |

Dry the chromatogram until smell of formic acid is gone. Cut off the end lanes of the chromatogram, soak the strips in ninhydrin solution and dry briefly. Amino acid spots of serine and cystathionine will develop.

Align the stained strips to the chromatogram, mark the cystathionine spot (spot closer to start), including about ½ cm of unstained area around the cystathionine spot. Cut out areas in each lane corresponding to the cystathionine standard put into a scintillation vial, add 5 ml of scintillation fluid and count, also include previous 5 μl samples.
The activity is calculated as follows:

[S], μmole=% Substrate consumed x serine concentration in assay mixture % Substrate consumed=CPM−blank/Total Counts Activity, U=[S] μmole incubation time (hour)

Specific Activity, U/mg=Activity/mg of enzyme in reaction mixture

2. An alternative embodiment

In an alternative embodiment in which ninhydrin is used instead of scintillation, the assay may be conducted as follows.
Procedure

| Enzyme Dilution Buffer |
| --- |
| 0.1M Tris pH 8.3 |
| 240 micromolar PLP |
| Reaction Cocktail |
| 0.154M Homocysteine |
| 0.099M Serine |

Dilute these components in 0.1M Tris at pH 8.3.

| Ninhydrin Reagent |
| --- |
| 333 mg Ninhydrin |
| 33.3 ml Acetic Acid Glacial |
| 11.1 ml Phosphoric Acid |

Stir well until Ninhydrin is completely dissolved.

| Cystathionine (CTT) Standards |
| --- |
| 31.25 mM CTT (range from 31.25 mM to 0.4883 mM) |

Make the dilution in 0.1N HCL
1.) Make serial dilution of the enzyme.
2.) Pipette 50 μL of serially diluted enzyme, followed by 50 μL of the reaction cocktail into wells of a micro titer plate (first plate), cover the plate.
3.) Incubate for 45 mins. at 37° C. while shaking.
4.) On a second micro titer plate (the final plate), prepare enzyme blanks by adding 200 μL of the ninhydrin reagent to wells followed by 6 μL of the reaction cocktail and 6 μL of the diluted enzyme.
5.) Remove the first plate from incubator and pipette 12 μL of each sample into the final plate. Also pipette 12 μL of serially diluted 31.25 mM CTT standard into the final plate.
6.) Immediately add 200 μL of the ninhydrin reagent to the samples and standards.
7.) Incubate the final plate for 10 minutes in a plate warmer at 95° C.
8.) Remove plate from plate warmer and place on ice for 5 minutes.
9.) Read the end point absorbance at 450 nm.
Calculations Draw the standard curve for the CTT standard samples. The equation for calculating the amount of CTT formed in micromoles/hr is:

[(S−B)/(A×Volume of sample in ml×Reaction time in hr)]×DF where
S=absorbance of the sample
B=absorbance of the blank
A=absorbance of 1 micromole of standard cystathionine.
DF=the dilution factor of the enzyme
Enzyme Units An enzyme unit is defined as the micromoles of cystathionine formed per hour under the assay conditions.

III. Homocysteine Assay Method
A. A First Embodiment

| Component | Concentration* |
| --- | --- |
| Trinder Reagent: | |
| Tris (pH 8.0) | 0.1M |
| 4-aminoantipyrine (4-AAP) | 1.6 mM |
| N-ethyl-N-(2 hydroxy-3-sulfopropyl)-m-toluidine (TOOS) | 1.6 mM |
| Thiamine pyrophosphate (TPP) | 0.77 mM |
| MgCl2 | 2.6 mM |
| KH2PO4 | 19.3 mM |
| Enzymes & Cofactors: | |
| BSA | 0.012 mg/mL |
| Pyridoxal 5' phosphate (PLP) | 0.1 mM |
| Peroxidase | 0.45 U/mL |
| pyruvate oxidase | 10.7 U/mL |
| CBL | 0.4 U/mL |
| CBS | 90 U/mL |
| Serine: | |
| Serine | 5 mM |

*Concentration is the final concentration in the Reagent

Enzymes and Cofactors are added to the Trinder reagent just prior to use. Enzymes and Cofactors are stored as stocks.
5 μL serine stock (230 mM) and 25 μL homocysteine containing Sample are added to reaction well.
200 μL of reagent (Trinder+Enzymes & Cofactors) is added to the serine and homocysteine containing sample.
Reaction is incubated at 37° C. (with mixing) for 20 minutes.
Color development is measured at 570 nm.

Figure 2:
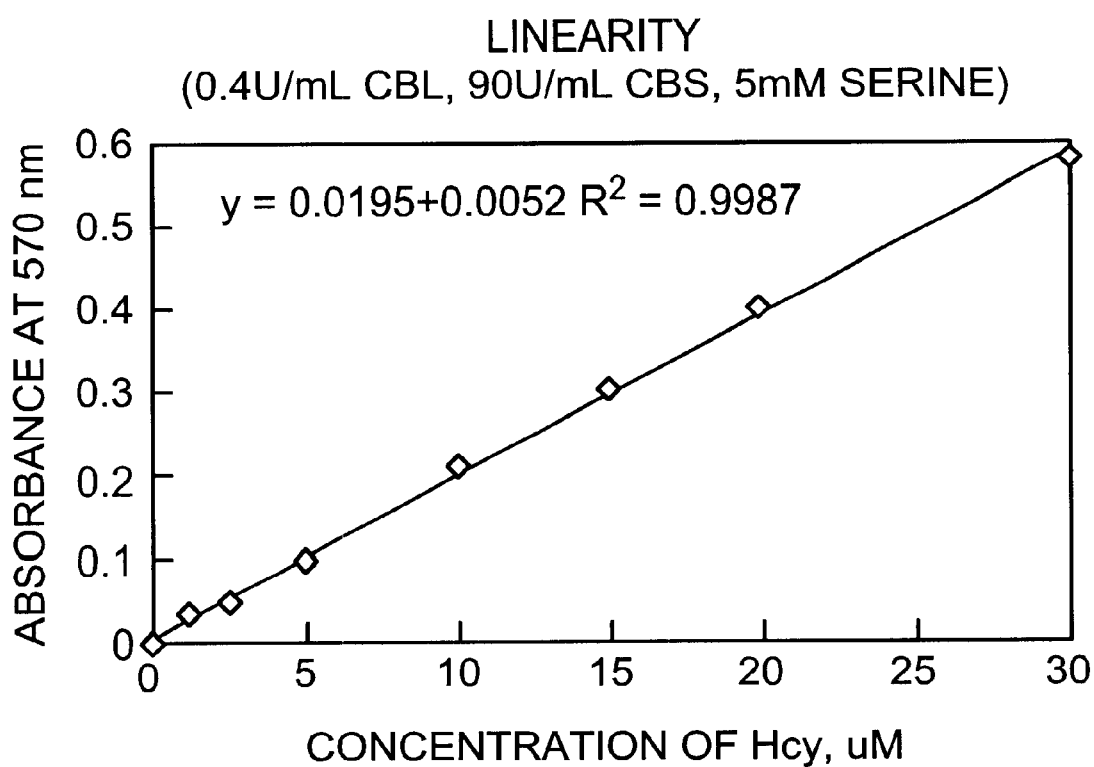
FIG. 2 illustrates the calculated linearity of homocysteine concentration as measured by pyruvate release according to assay method of the invention.

The calculated linearity of homocysteine concentration is shown in FIG. 2. In this figure, the absorbance of released pyruvate is shown against the concentration of homocysteine.

B. A Second Embodiment

Plasma and/or serum samples containing homocysteine were reduced using 2.5 mM DTT in the buffer containing 12.5 mM sodium citrate buffer at pH 7.8, 1% Triton, and 0.5 mM EDTA. The treated solution was capped and incubated for 20 minutes at 25° C. then was uncapped and placed on the analyzer wheel. 20 microliters of sample and 5 microliters of water were added to 72 microliters of Reagent 1 and 92 microliters of Reagent 2. Reagent 1 was added at time point T1(0 minutes), and Reagent 2 was added at T2 (about 20 seconds afterwards). Read points were at 25 and 50 (about 8 minutes). The assay was read at 550 nm, using the Cobas Mira analyzer.

Reagent composition was as follows:

| R1 Reagent Composition | R2 Reagent Composition |
|---|---|
| 2.56 mM serine | 2.42 U/mL CBL |
| 1.15 U/mL peroxidase | 0.2 mM PLP |
| 27.3 U/mL pyruvate oxidase | 360 U/mL CBS |
| 10 mg/mL BSA | 10 mg/mL BSA |
| 127.8 mM Tris buffer at pH 7.8 | 100 mM Tris buffer at pH 7.8 |
| 6.6 mM $MgCl_2$ | 3.2 mM TOOS |
| 3.4 mM 4-AAP | 80 mg/ml Gentamycin |
| 49.3 mM $KH_2PO_4$ | |
| 1.97 mM TPP | |
| 80 mg/ml Gentamycin | |

Results obtained with the above-described assay, as compared to the use of HPLC and standardized sampled samples of homocysteine, are as follows. The automated HPLC procedure for measuring homocysteine was conducted in accordance with T. Fiskerstrand, H. Refsum, G. Kvalheim, and P. M. Ueland, *Clin Chem* 39:263–271 (1993) As these results show, the assay of the invention provides accurate determinations of homocysteine concentration in patient samples, as compared to the HPLC automated procedure that has been used in the art as a standard for homocysteine quantification analysis.

Homocysteine

Cobas Mira vs HPLC

Mira was calibrated with homocysteine (HCY) Control (BioRad 10) at 10 micromoles/L. All samples were reduced before assay. For the purposes of the chart below, "umol/L" shall be understood to mean micromoles per liter.

| Sample | HCY (umol/L) Genzyme MIRA | HCY (umol/L) PBI HPLC | Difference (umol/L) Genzyme - HPLC | % Difference Genzyme - HPLC |
|---|---|---|---|---|
| 4 | 7.63 | 6.60 | −1.03 | −15.6% |
| 5 | 10.54 | 11.40 | 0.86 | 7.5% |
| 10 | 8.16 | 9.50 | 1.34 | 14.1% |
| 16 | 9.30 | 9.70 | 0.40 | 4.1% |
| 17 | 7.47 | 7.10 | −0.37 | −5.2% |
| 18 | 7.23 | 8.50 | 1.27 | 15.0% |
| 24 | 6.73 | 8.10 | 1.37 | 16.9% |
| 26 | 7.93 | 9.60 | 1.68 | 17.4% |
| 29 | 6.72 | 6.70 | −0.02 | −0.4% |
| 30 | 6.96 | 8.20 | 1.24 | 15.1% |
| 35 | 7.37 | 5.80 | −1.57 | −27.1% |
| 38 | 8.28 | 9.70 | 1.42 | 14.6% |
| 44 | 7.57 | 8.70 | 1.13 | 13.0% |
| 45 | 7.40 | 8.10 | 0.71 | 8.7% |
| 49 | 7.06 | 7.50 | 0.45 | 5.9% |
| 50 | 5.25 | 5.20 | −0.05 | −0.9% |
| 57 | 6.15 | 7.90 | 1.76 | 22.2% |
| BIORAD10 | 9.69 | 10.00 | 0.31 | 3.1% |
| Mean | 7.64 | 8.24 | 0.60 | 6.0% |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining the concentration of homocysteine in a sample, comprising the steps of:
   a) contacting the sample with serine, cystathionine B-synthase and cystationine B-lyase;
   b) determining the concentration of at least one of pyruvate or ammonia produced in step (a),
   wherein the concentration of said pyruvate or ammonia can be correlated to the concentration of homocysteine in the sample.

2. The method of claim 1, further comprising contacting the sample with a reducing agent.

3. The method of claim 2, wherein the step of contacting the sample with a reducing agent is conducted prior to step (a).

4. The method of claim 2, wherein said reducing agent is provided in a concentration of less than about 30 millimolar.

5. The method of claim 2, wherein said reducing agent is provided in a concentration of about 2 to about 10 millimolar.

6. The method of claim 2, wherein the sample is allowed to incubate with the reducing agent for about 10 minutes at a temperature of about 37° C.

7. The method of claim 2, wherein the sample is allowed to incubate with the reducing agent for about 20 minutes at a temperature of about 25° C.

8. The method of claim 1, wherein step (a) further comprising contacting the sample with an enzyme co-factor.

9. The method of claim 8, wherein said enzyme co-factor is pyridoxal 5' phosphate.

10. The method of claim 8, wherein said enzyme co-factor is provided in a concentration of about 0.2 micromolar.

11. The method of claim 1, wherein the concentration of pyruvate is determined by contacting the sample with one or more reagents for the colormetric determination of pyruvate contains a material selected from the group consisting of pyruvate oxidase and lactate dehydrogenase.

12. The method of claim 1, wherein the concentration of ammonia is determined by contacting the sample with one or more reagents for the colormetric determination of ammonia.

13. The method of claim 1, wherein following step (a) the sample is allowed to incubate for about 10 to about 20 minutes prior to determining the concentration of pyruvate or ammonia.

14. The method of claim 1, wherein the rate of release of pyruvate is correlated with standard concentration values for homocysteine.

15. A method of determining the concentration of homocysteine in a sample comprising the steps of:
   a) contacting the sample with a first reagent comprising serine;
   b) contacting the sample with a second reagent comprising CBS and CBL; and
   c) determining the concentration pyruvate produced, wherein the concentration of pyruvate can be correlated to the concentration of homocysteine in the sample.

16. The method of claim 15, wherein the first reagent further comprises pyruvate oxidase.

17. The method of claim 15, wherein the second reagent further comprises an enzyme co-factor.

18. The method of claim 16, wherein the enzyme co-factor is pyridoxal 5' phosphate.

19. The method of claim 15, wherein prior to step (a) the sample is contacted with a third reagent containing a reducing agent.

20. The method of claim 19, wherein the sample is allowed to incubate with the third reagent for 10 minutes at 37° C. prior to step (a).

* * * * *